(12) United States Patent
Hyun et al.

(10) Patent No.: US 9,931,279 B2
(45) Date of Patent: Apr. 3, 2018

(54) NEONATAL FLUID TUBING HEATER

(71) Applicant: Acacia, Inc., Brea, CA (US)

(72) Inventors: Dongchul D. Hyun, Brea, CA (US); Michael T. Fleury, Brea, CA (US)

(73) Assignee: MEDELA HOLDING AG, Baar (CH)

( * ) Notice: Subject to any disclaimer, the term of this patent is extended or adjusted under 35 U.S.C. 154(b) by 0 days.

(21) Appl. No.: 14/222,832

(22) Filed: Mar. 24, 2014

(65) Prior Publication Data

US 2014/0207063 A1 Jul. 24, 2014

Related U.S. Application Data

(63) Continuation-in-part of application No. 14/154,785, filed on Jan. 14, 2014, now abandoned, which is a continuation of application No. 13/092,582, filed on Apr. 22, 2011, now Pat. No. 8,663,161.

(51) Int. Cl.
| | |
|---|---|
| *A61F 7/12* | (2006.01) |
| *A61J 15/00* | (2006.01) |
| *A61M 5/44* | (2006.01) |
| *A61M 5/145* | (2006.01) |
| *A61G 7/05* | (2006.01) |

(52) U.S. Cl.
CPC ............ *A61J 15/0026* (2013.01); *A61M 5/44* (2013.01); *A61G 7/0503* (2013.01); *A61J 2200/42* (2013.01); *A61M 5/1456* (2013.01); *A61M 2205/3368* (2013.01); *A61M 2205/36* (2013.01); *A61M 2205/3653* (2013.01); *A61M 2205/8206* (2013.01); *A61M 2210/1042* (2013.01); *A61M 2240/00* (2013.01)

(58) Field of Classification Search
CPC .. A61M 5/44; A61M 2205/3653; A61M 1/28; A61M 5/445; A61M 1/288; A61M 2205/3368; A61M 1/284
USPC ..... 604/890.1–892.01, 113–114, 65–67, 131
See application file for complete search history.

(56) References Cited

U.S. PATENT DOCUMENTS

| | | | | |
|---|---|---|---|---|
| 3,371,975 | A | * | 3/1968 | Meltzer ...................... 55/385.1 |
| 4,532,414 | A | * | 7/1985 | Shah et al. ..................... 392/470 |
| 4,680,445 | A | * | 7/1987 | Ogawa ................... A61M 5/44 |
| | | | | 165/46 |

(Continued)

FOREIGN PATENT DOCUMENTS

| | | |
|---|---|---|
| CN | 201139844 | 10/2008 |
| CN | 201814947 | 5/2011 |

OTHER PUBLICATIONS www.paragonmed.com; "Fluid Warmers"; Feb. 10, 2011; 3 pages.

(Continued)

*Primary Examiner* — Phillip Gray
(74) *Attorney, Agent, or Firm* — Stetina Brunda Garred and Brucker

(57) ABSTRACT

A heating system for heating neonate nutritional liquid, including a heater and a control module. The heater includes a heating portion having serpentine shaped grooves for receiving a tube. The tube may be a serpentine feeding tube module, having a serpentine tube portion, or a serpentine feeding tube cassette, having a serpentine tube portion covered by a rigidly attached polymeric sheet. The serpentine feeding tube cassette may include a thermocouple to measure the temperature of the warmed nutritional liquid as it exits the cassette.

21 Claims, 10 Drawing Sheets

(56) References Cited

U.S. PATENT DOCUMENTS

| | | |
|---|---|---|
| 5,250,032 A | 10/1993 | Carter et al. |
| 7,158,719 B2 | 1/2007 | Cassidy |
| 8,663,161 B2 | 3/2014 | Hyun et al. |
| 2004/0073161 A1 | 4/2004 | Tachibana |
| 2005/0008354 A1 | 1/2005 | Cassidy |
| 2005/0209563 A1 | 9/2005 | Hopping et al. |
| 2008/0119782 A1 | 5/2008 | Steinman et al. |
| 2008/0262409 A1 | 10/2008 | Derrico et al. |
| 2012/0271271 A1 | 10/2012 | Hyun et al. |
| 2013/0237957 A1 | 9/2013 | Hyun et al. |
| 2014/0128845 A1 | 5/2014 | Hyun et al. |

OTHER PUBLICATIONS www.ncbi.nlm.nih.gov; "Effect of Enteral Feeding Temperature on Feeding Tolerance in Preterm Infants"; Dec. 31, 2010; 1 page.

www.zawya.com; "Ge Healthcare's New Transportable Power Source Showcased at Arab Health Strenthens Neonatal Care"; Jan. 28, 2011; 4 pages.

Copenheaver, Blaine R., PCT Notification of Transmittal of the International Search Report and the Written Opinion of the International Searching Authority of the Declaration,dated Jul. 24, 2014, pp. 1-13.

\* cited by examiner

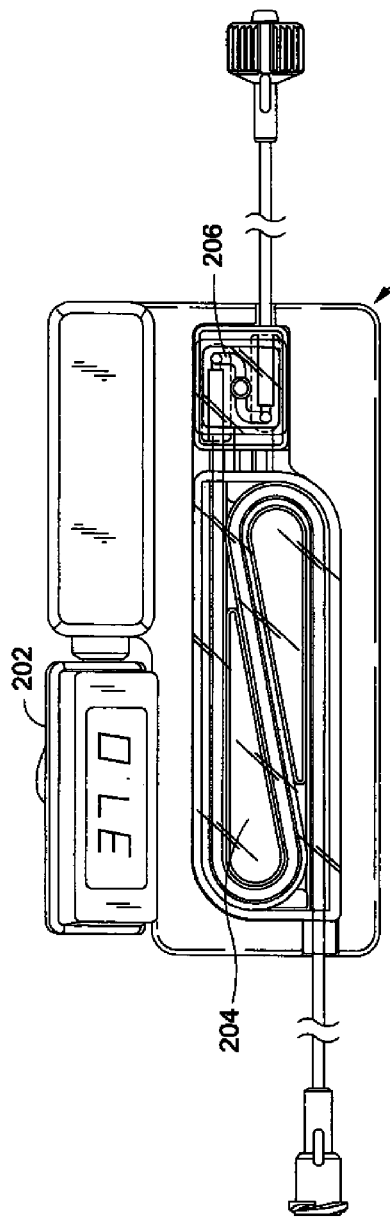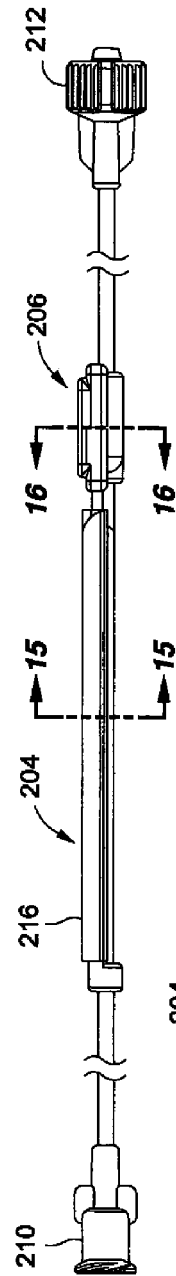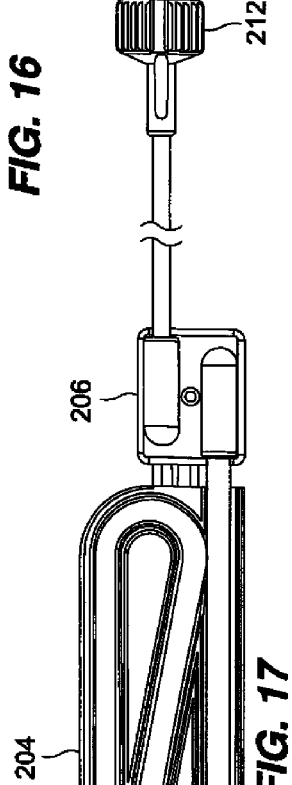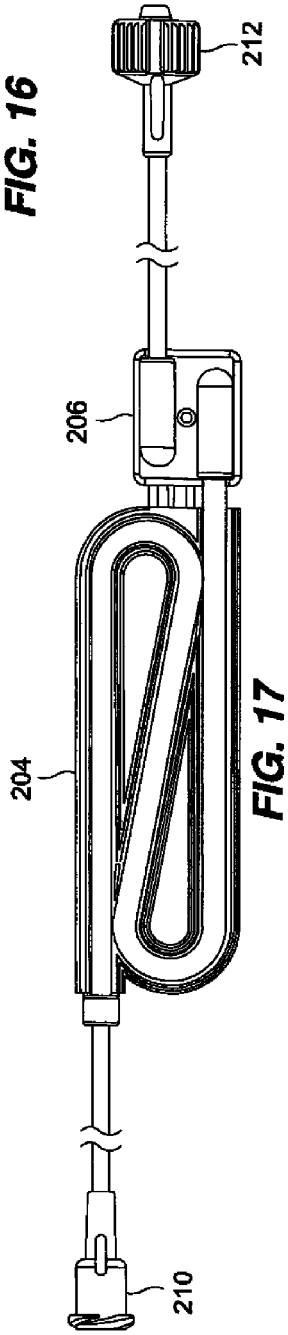
FIG. 13
FIG. 14
FIG. 16
FIG. 17
FIG. 15

NEONATAL FLUID TUBING HEATER

CROSS-REFERENCE TO RELATED APPLICATIONS

This application is a continuation-in-part of U.S. application Ser. No. 14/154,785 filed Jan. 14, 2014 which is a continuation of U.S. application Ser. No. 13/092,582 filed Apr. 22, 2011, the entirety of the disclosures of which are expressly incorporated herein by reference.

STATEMENT RE: FEDERALLY SPONSORED RESEARCH/DEVELOPMENT

Not Applicable

BACKGROUND

The embodiments disclosed herein relate to a heater for warming nutritional liquid fed to a pre-term infant.

Nutritional delivery to a preterm infant or enteral feeding is an important part of caring for the preterm infant in neonate-natal intensive care units. Typically, the preterm infant is fed with a feeding tube that delivers breast milk or neonatal formula directly into the stomach of the preterm infant. The feeding tube is generally introduced either through the nose (i.e., nasally) or through the mouth (i.e., gastrically). Previously, the breast milk or neonatal formula was fed to the neonate while the breast milk or neonate formula was at room temperature (i.e., below body temperature). However, studies have shown that preterm infants respond favorably when the nutritional liquid (e.g., breast milk or neonatal formula) coincides with the body temperature of a person (i.e., 98.6° F.). When the nutritional liquid is provided to the preterm infant at a temperature closer to the body temperature of a person, the preterm infant was found to digest more of the nutritional liquid. Moreover, other studies have found that the lower the body temperature of the preterm infant, the higher the likelihood of mortality of the preterm infant. As such, it is important to preserve the preterm infant's energy so that the preterm infant does not need to divert energy away from heating and growth to generate heat. If the nutritional liquid is fed to the preterm infant at room temperature, the preterm infant must divert energy that could be used for healing and growth to heat him or herself due to digestion of the cold nutritional liquid. Accordingly, it would be beneficial to feed preterm infants with nutritional liquid raised to the body temperature of a person to reduce the amount of energy diverted away from healing and growth to digestion and heat generation.

In response, prior art devices have been introduced for warming nutritional liquid (e.g., breast milk or neonate formula) provided to pre-term infants. Typically, the nutritional liquid is warmed in a neonate feeding syringe or warm nutritional liquid is poured into the syringe and then fed to the neonate. Unfortunately, even if the nutritional liquid is pre-warmed to body temperature, the temperature of the nutritional liquid in the feeding syringe decreases to room temperature during feeding due to the long feeding time. The average feeding time is about 30 minutes to 4 hours. Heat is lost through the neonate feeding syringe. Also, heat is lost through a tube routed to the stomach of the neonate. In particular, as the nutritional liquid flows from the feeding syringe to the neonate through the tube, significant heat loss is experienced through the tubing since the nutritional liquid travels through the tubing at a relatively slow rate. Accordingly, even if the nutritional liquid in the neonate feeding syringe is raised to the body temperature of the mother, such warming is rendered ineffective since there is a significant temperature drop as the nutritional liquid flows through the tube.

Accordingly, there is a need in the art for an improved method and device for heating nutritional liquid fed to the pre-term infant.

BRIEF SUMMARY

The embodiments discussed herein address the needs discussed above, discussed below and those that are known in the art.

A heating system that includes a heater and a control module is disclosed herein. The control module controls operation of the heater. The heater is used to warm the nutritional liquid (e.g., breast milk or neonate formula) being fed to the neonate. In particular, the heater of the heating system is placed in close proximity to the neonate along a length of a tube being used to feed the neonate. Since the heater is in close proximity to the neonate on the tube, the temperature drop due to heat loss through the tube after the nutritional liquid is heated and travels to the neonate is minimal. Moreover, any heat loss from the syringe to the heater is inconsequential since the heater raises the temperature of the nutritional liquid to the desired target temperature immediately before the nutritional liquid reaches the neonate.

More particularly, a heating system for heating neonate nutritional liquid so that a temperature of the nutritional liquid is greater than room temperature when providing warmed nutritional liquid to the neonate during feeding is disclosed. The heater system may comprise a heater including a first heating portion having a first groove for receiving a tube; a first handle fixed to the first heating portion; a second portion disposable over the first groove; and a second handle fixed to the second portion.

The first heating portion and handle may be pivotally traversable to the second portion and handle between open and closed positions. In the open position, the neonate feeding tube may be inserted or removed from the first groove. In the closed position, the second portion covers the first groove and the first heating portion warms the neonate nutritional liquid that flows through the tube.

The second portion may have a heating portion and a second groove for receiving the tube. The first and second grooves may collectively have a snug fit around the tube for transferring heat through the neonate feeding tube to the neonate nutritional liquid flowing through the neonate feeding tube. The first heating portion may comprise a first heater and a first heat conductor. The first groove may be formed in the first heat conductor. The second heating portion comprises a second heater and a second heat conductor. The second groove may be formed in the second heat conductor.

The first and second grooves may be straight and have matching semi-circular cross sectional configurations.

The first and second portions may be pivotally biased to the closed position. A spring may bias the first and second portions to the closed position.

The heating system may further comprise a control module including a rechargeable battery pack for providing electricity to the heater and a means for controlling the heater. The control module may include a readout for providing a temperature of the heater. The control module may also include a battery strength indicator. The control module and the heater may be in electrical communication with each other through a wire. The control module may be integrated into a body of the heater.

Additionally, a system for providing warm nutritional liquid to a neonate is disclosed. The system may comprise a neonate feeding syringe fillable with the nutritional liquid; a tube connected to the syringe and in fluid communication with a stomach of the neonate; a syringe pump wherein the syringe is mountable to the syringe pump which forces the nutritional liquid from the syringe through the tube to the neonate; a heater mounted about the tube and positioned closer to the neonate than the syringe pump along a length of the tube wherein the heater transfers heat through the tube and to the nutritional liquid flowing through the tube to minimize heat loss from the nutritional liquid after the nutritional liquid exits the heater and flows toward the neonate so that the nutritional liquid is provided to the neonate above room temperature.

The tube may be an extension tube and the heater may be positioned immediately adjacent to a distal end of the extension tube. The heater may abut the distal end of the extension tube.

The system may further comprise a feeding tube in fluid communication with the extension tube and the heater further. The heater may comprise a first heating portion having a first groove for receiving the extension tube; a first handle fixed to the first heating portion; a second portion disposable over the first groove; a second handle fixed to the second portion.

The first heating portion and handle may be pivotally traversable to the second portion and handle between open and closed positions. In the open position, the feeding tube or extension tube may be inserted or removed from the first groove. In the closed position, the second portion covers the first groove and the first heating portion warms the neonate nutritional liquid that flows through the extension tube or the neonate feeding tube.

Additionally, a system for providing warm nutritional liquid to a neonate is disclosed. The system may comprise a gravity feeding syringe fillable with the nutritional liquid; a tube connected to the syringe and in fluid communication with a stomach of the neonate; a stand for hanging the gravity feeding syringe above the neonate to flow the nutritional liquid from the syringe through the tube to the neonate; a heater mounted about the tube and positioned closer to the neonate than the syringe pump along a length of the tube. The heater transfers heat through the tube and to the nutritional liquid flowing through the tube to provide warm nutritional liquid to the neonate to minimize heat loss from the nutritional liquid after the nutritional liquid exits the heater and flows toward the neonate so that the nutritional liquid is provided to the neonate above room temperature.

The tube may be a feeding tube and the heater may be positioned immediately adjacent to the neonate so that a temperature of the nutritional liquid is above room temperature when the nutritional liquid reaches the neonate.

Additionally, a method of feeding a neonate with warm nutritional liquid is disclosed. The method may comprise the steps of filling a neonate feeding syringe with nutritional liquid; connecting a tube to the neonate feeding syringe; placing the tube in fluid communication with a stomach of the neonate; placing a heater on the tube for heating the nutritional fluid flowing through the tube, the heater being positioned on the tube closer to the neonate than the neonate feeding syringe along a length of the tube; flowing the nutritional liquid from the neonate feeding syringe, through the tube and to the neonate; and heating the nutritional liquid flowing through the tube with the heater so that a temperature of the nutritional liquid is above room temperature when the nutritional liquid reaches the neonate to facilitate digestion of the warm nutritional liquid by the neonate.

The flowing step may be accomplished with a syringe pump. The flowing step may also comprise elevating the neonate feeding syringe above the neonate to gravity feed the neonate.

Additionally, an alternative embodiment of a heating system for heating neonate nutritional liquid is disclosed. The heating system includes a heater and a control module. The heater includes a heater base, a heating portion having serpentine shaped grooves for receiving a tube, and a heater cover rotatably connected to the heater base. The heating portion is located within the heater base. The control module includes a means for controlling the heater.

The heater may further include a microswitch positioned such that the microswitch is depressed when the heater cover is in a closed position abutting the heater base. In particular, the heater may only operate when the microswitch is depressed. The heater may further include an operating indicator that may illuminate when the microswitch is depressed. The heater may further include a thermocouple for monitoring the temperature of the heating portion. The heater may also further include a thermal cutoff, to cease operation of the heater if it exceeds normal operating temperatures in case of a control module failure.

The control module may include a display capable of presenting information about the heater's operation. The control module may be in electrical communication with the heater through a control cable, or the control module may be integrated directly into the heater.

The tube may be configured as a serpentine shaped feeding tube module. In this embodiment, the serpentine shaped feeding tube module includes a serpentine configured tube portion complementarily shaped to the pattern of the serpentine grooves formed in the heater, and further includes a proximal connector on one end and a distal connector on the opposite end. The proximal connector may be fluidly connectable to a nutritional liquid source and the distal connector may be fluidly connectable to a feeding tube positioned in fluid communication with a stomach of the neonate.

Another embodiment of a heating system for heating neonate nutritional liquid is also disclosed, wherein the system includes a heater and a control module. In this embodiment, the heater includes a heating portion having serpentine shaped grooves for receiving a feeding tube cassette. The control module may be directly integrated into the heater. In this embodiment, a feeding tube cassette has a serpentine tube portion configured to match the pattern of the serpentine grooves formed in the heater, which is located between a proximal connector and a distal connector. A polymeric sheet is rigidly attached to and covers the serpentine tube portion. The serpentine feeding tube cassette may further include a thermocouple located between the serpentine tube portion and the distal connector. The thermocouple may be configured to measure the temperature of the warmed nutritional liquid as it exits the cassette. The thermocouple may be in electric communication with the control module.

Also disclosed is a system for providing warm nutritional liquid to a neonate. The system includes a neonate nutritional liquid source, a feeding tube in fluid connection with the nutritional liquid source and a stomach of the neonate, and a heater mounted about the feeding tube. The feeding tube includes a serpentine configured feeding tube portion positioned closer to the neonate than the nutritional liquid source, and the heater is mounted about this serpentine shaped feeding tube portion. The serpentine feeding tube portion may be formed as a feeding tube module and the heater may include a heating portion having serpentine shaped grooves located within a base of the heater for receiving the feeding tube module, and a heater cover. Alternatively, the serpentine shaped feeding tube portion may be a serpentine feeding tube cassette having a thermocouple and a polymeric sheet rigidly attached to the serpentine shaped feeding tube portion. In this embodiment, the heater may include a heating portion having serpentine shaped grooves for receiving the serpentine feeding tube cassette.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 13 is a top view of the heater shown in FIG. 12;

FIG. 14 is a side view of the feeding tube cassette;

FIG. 15 is a cross-sectional view of the feeding tube cassette of FIG. 15;

FIG. 16 is a cross-sectional view of a thermocouple of the feeding tube cassette; and FIG. 17 is a bottom view of the feeding tube cassette.

DETAILED DESCRIPTION

Figure 1:
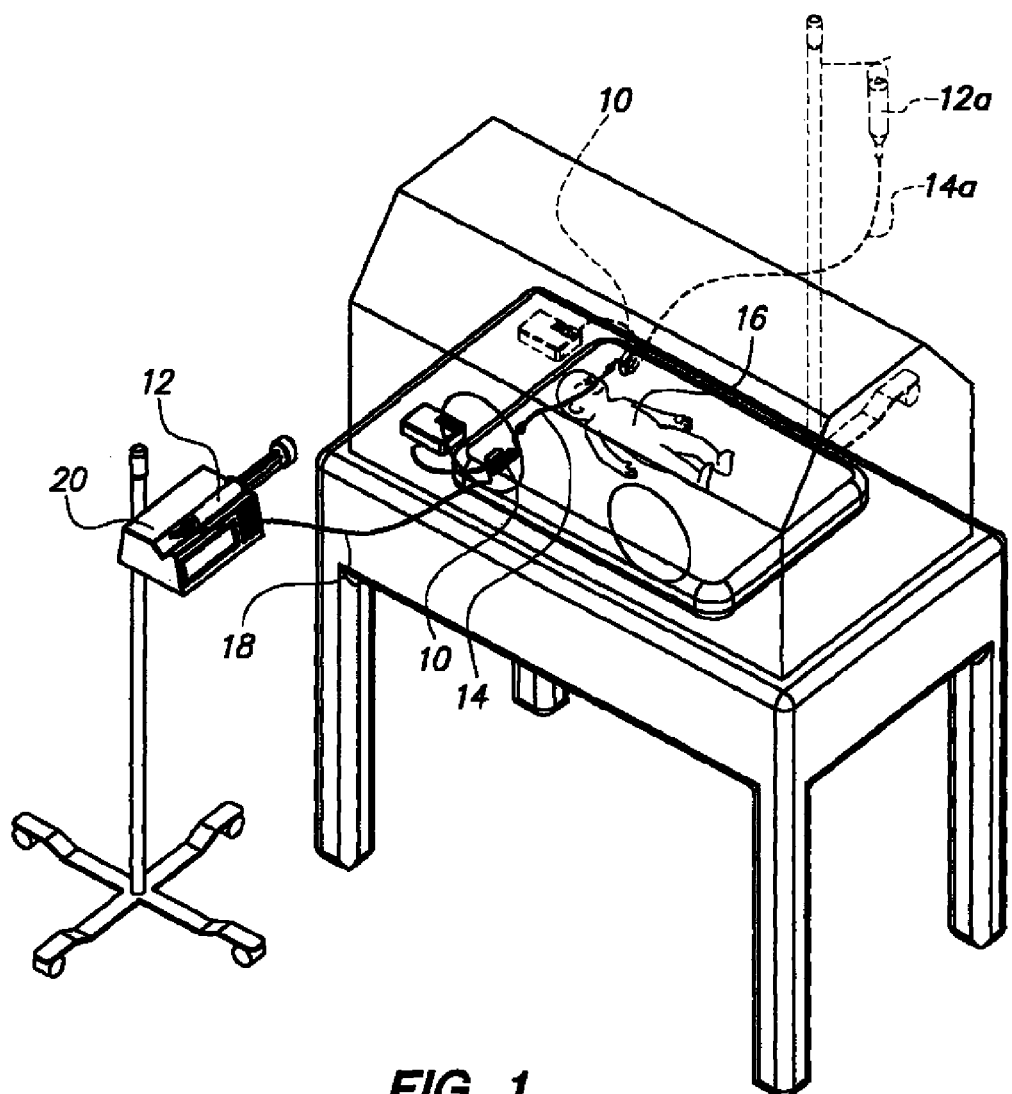
FIG. 1 illustrates a neonate being fed with a syringe pump or alternatively with a gravity syringe and a heating system disposed as close to the neonate so that the neonate is fed with nutritional liquid above room temperature and preferably at normal body temperature of a person.

Referring now to the drawings, an in-line neonatal fluid tubing heater 10, 10a is shown. A syringe 12, 12a is filled with a nutritional liquid (e.g., breast milk or neonate formula). From the syringe 12, 12a, the nutritional liquid flows through extension tube 18 and feeding tube 14 or feeding tube 14a. The heater 10 is mounted to the extension tube 18 or the feeding tube 14a to warm up the nutritional liquid flowing through the feeding tube 14, 14a above room temperature and preferably to about the body temperature of a person (i.e. between about 95° F. and about 99° F.). Feeding warm nutritional liquid to the neonate 16 facilitates digestion of the nutritional liquid and preserves the neonate's energy for healing and growth. The heater 10, 10a may be placed on the extension tube 18 or the tube 14a as close to the neonate 16 as possible to minimize a reduction in the temperature of the nutritional fluid as the nutritional liquid exits the heater 10, 10a on its way to the neonate 16. As the nutritional liquid flows through the heater 10, the heater 10 increases the temperature of the nutritional liquid to a temperature above room temperature and preferably to a temperature about the body temperature of the neonate 16.

As shown in FIG. 1, the neonate 16 may be fed nutritional liquid with a syringe 12 and syringe pump 20 or with a gravity syringe 12a. In relation to the syringe pump 20, the heater 10 is shown as being attached to the extension tube 18 instead of the feeding tube 14. However, it is also contemplated that the heater 10 may be mounted to the feeding tube 14 as close as possible to the neonate 16 in a similar fashion as the heater 10 described in relation to the gravity feeding method.

Figure 2:
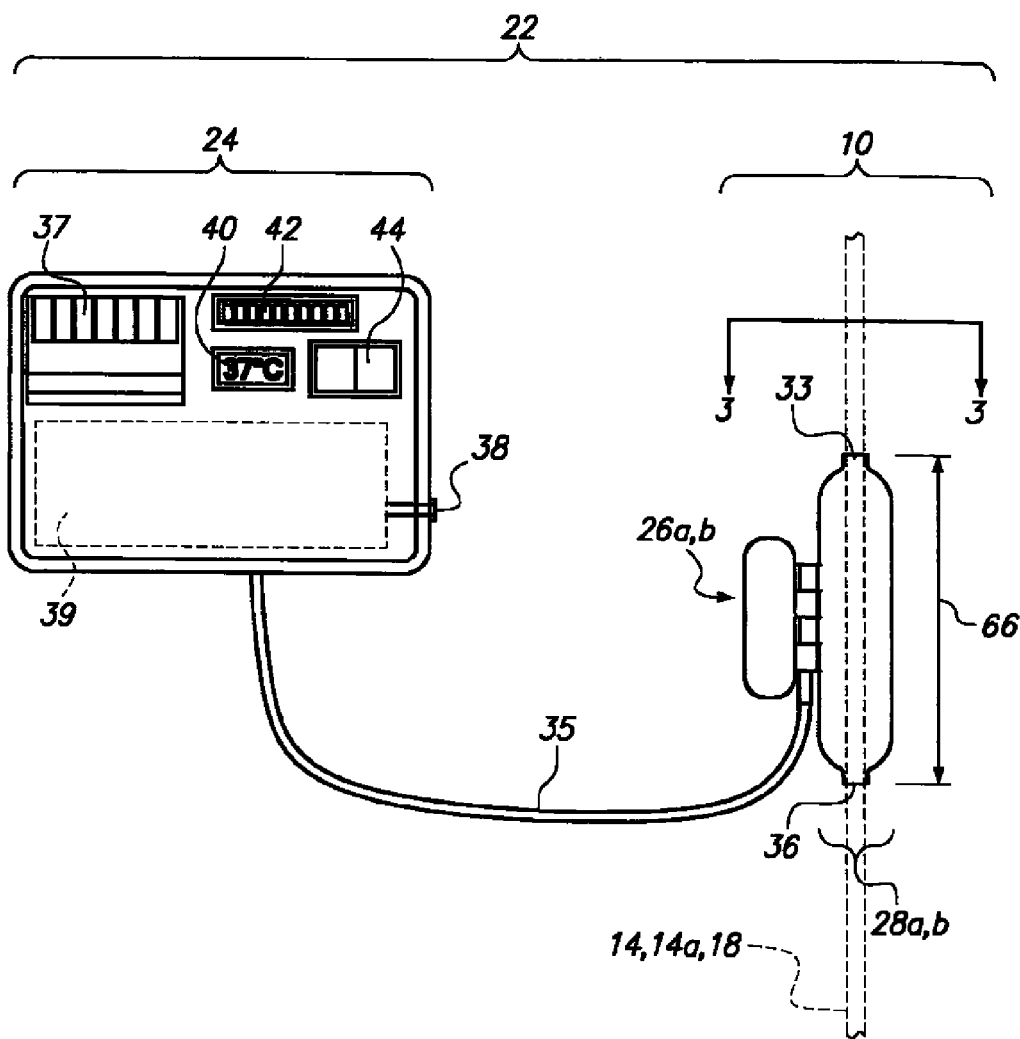
FIG. 2 illustrates the heating system having a heater and a control module.
Figure 3:
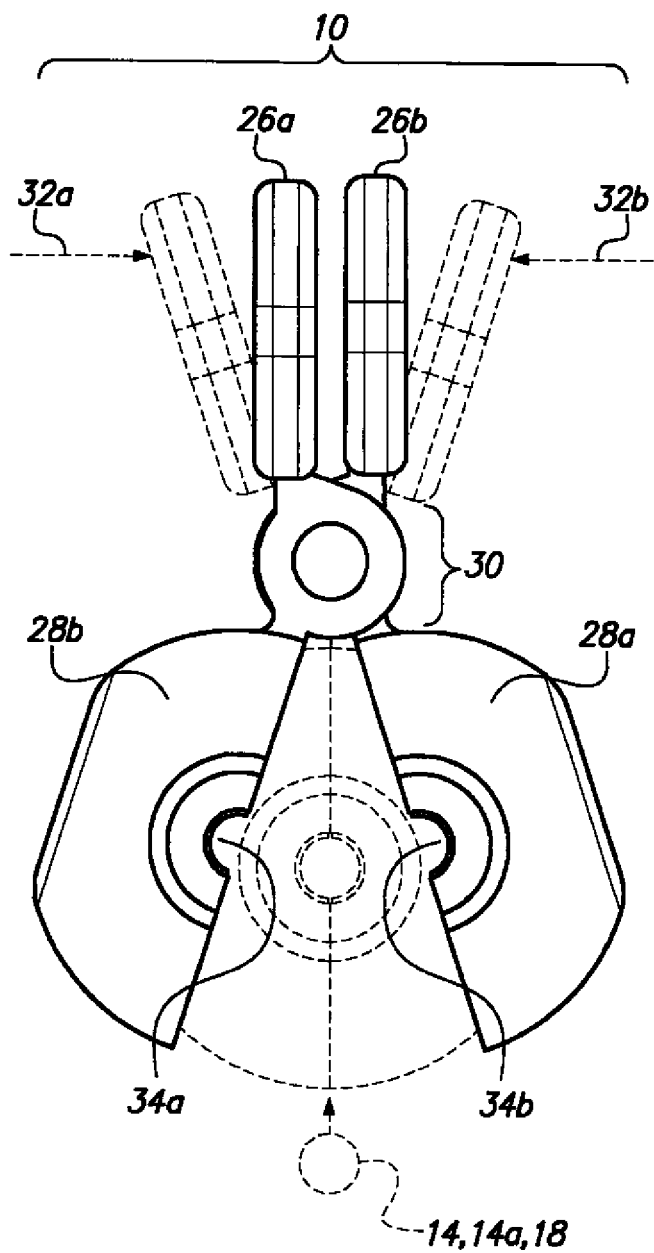
FIG. 3 is a side view of the heater shown in FIG. 2.

A heating system 22 is shown in FIG. 2. The heating system 22 may comprise the heater 10 and a control module 24. The heater 10 is shown in more detail in FIGS. 3 and 4. Referring to FIG. 3, the heater 10 may be traversed between the open and closed positions. The open position is shown in solid lines in FIG. 3. The closed position is shown in dash lines in FIG. 3. The first and second handles 26a, b and first and second heating portions 28a, b may be biased to the closed position as shown in dash lines in FIG. 3. The handles 26a, b and heating portions 28a, b may be biased to the closed position by way of a torsion spring 63 (see FIG. 4) fitted within hinge 30. From the closed position shown by the dash lines, a person may grip the first and second handles 26a, b and apply opposing compressive forces 32a, b to overcome the biasing force and open the first and second heating portions 28a, b. The feeding tube 14, 14a or extension tube 18 may be fitted within the heating portions 28a, b to heat nutritional liquid that flows through the tubes 14, 14a, 18. When the tubes 14, 14a, 18 are fitted within the first and second heating portions 28a, b, the user may release the first and second handles 26a, b to clamp the first and second heating portions 28a, b about the tube 14, 14a, 18. Each of the heating portions 28a, b may have a straight elongated groove 34a, b that extends along the length 66 of the heating portions 28a, b as shown in FIGS. 2 and 3. The heating portions 28a, b may be sufficiently long so that heat can be transferred into the nutritional liquid as the nutritional liquid flows through the tube 14, 14a, 18 between an entrance 33 and exit 36 (see FIG. 2) of the heating portions 28a, b. The heater 10 may also be in electrical communication with the control module 24 through cable 35. The control module 24 is capable of controlling the heating portions 28a, b by way of heater controller 37. The heater 10 and the control module 24 may be powered by rechargeable batteries 39. The rechargeable batteries 39 may be recharged by way of a charger connected to a battery recharge port 38. A readout 40 (e.g., digital readout) provides the temperature of the heating portions 28a, b. Battery strength/charging indicator 42 may also be provided on the control module 24. The control module 24 and the heater 10 may be turned on and off by way of an on/off switch 44.

During use, the operator squeezes the handles 26a, b together to traverse the heater 10 to the open position as shown in FIG. 3. With the heater 10 in the open position, the operator inserts the tube 14, 14a, 18 into the first and second grooves 34a, b. In particular, the tube 14, 14a, 18 is inserted into one of the grooves 34a, 34b. Once the tube 14, 14a, 18 is placed in the groove 34a or 34b, the operator releases the first and second handles 26a, b to traverse the heater portions 28a, b to the closed position. In the closed position, the tube 14, 14a, 18 is nested within the grooves 34a, b. Preferably, the heater portions 28a, b contact and press against tube 14, 14a and 18 to provide as much heat to the nutritional liquid flowing through the tube 14, 14a, 18.

Referring now to FIG. 2, once the tube 14, 14a, 18 is placed in the heater 10, the operator turns on the control module 24 by toggling switch 44 to the on position. The user adjusts the temperature at which the heater 10 will heat the nutritional liquid by manipulating buttons of the heater controller 37. The operator either increases or decreases the maximum temperature of the heater 10. The maximum temperature is shown on the readout 40. The heater 10 and the control module 24 have a feedback loop which allows the control module 24 to control the maximum temperature of the heater 10. Additional toggle buttons and/or readouts 40 may be mounted to the control module 24 so that the readouts 40 can also provide the current temperature of the heater 10. Additional temperature sensors may be mounted to the heater 10, 10a to sense a temperature of the nutritional fluid flowing through the tube 14, 14a, 18. The control module 24 and the heater 10 are portable in that the control module 24 and the heater 10 may be powered by a battery pack 39. The remaining power in the battery pack 39 may be indicated by indicator 42. Also, the battery pack 39 may be recharged by connecting the battery pack 39 to a battery charger by way of recharge port 38.

Figure 4:
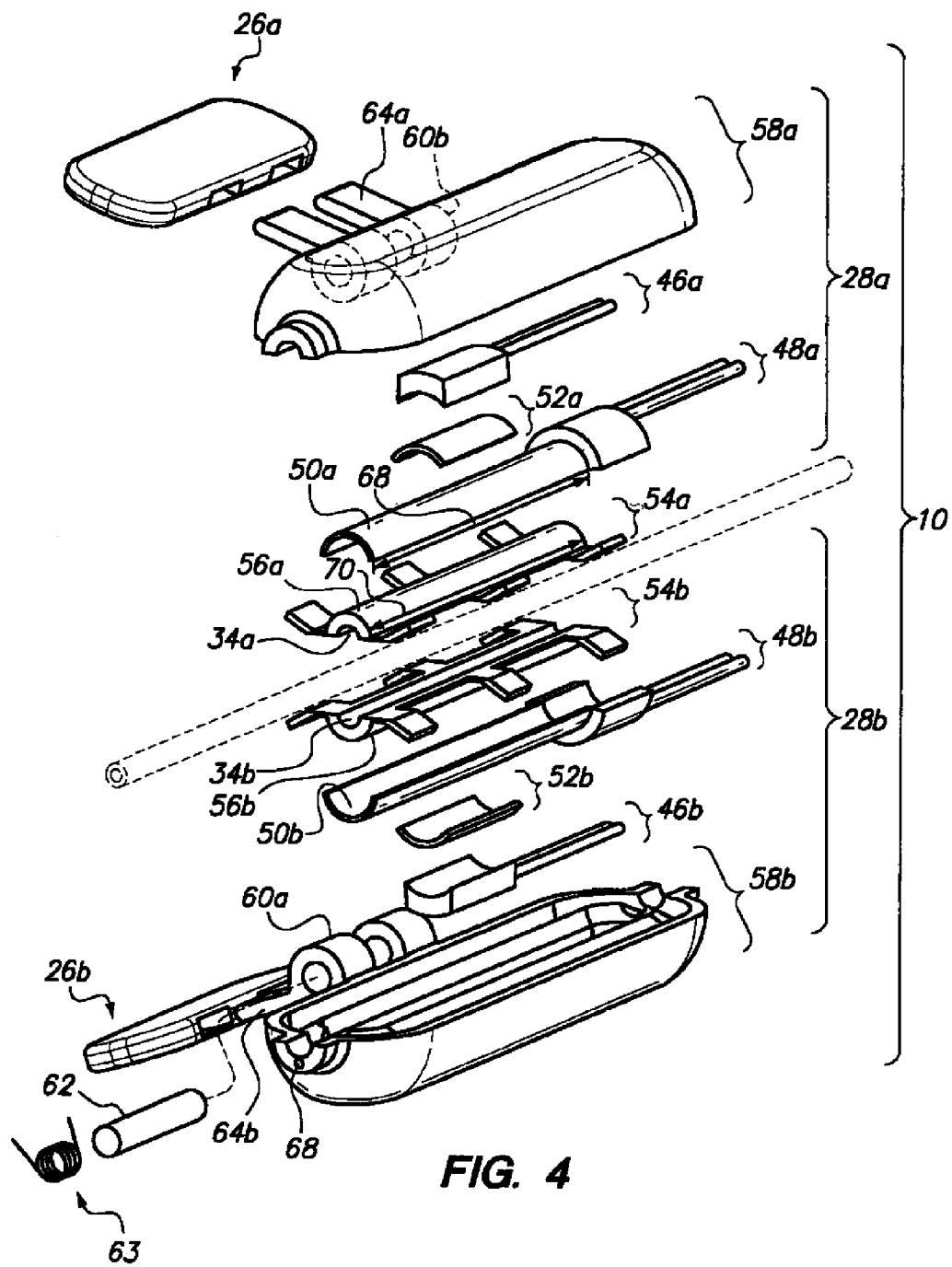
FIG. 4 is an exploded perspective view of the heater shown in FIGS. 1-3.

Referring now to FIG. 4, an exploded view of the heater 10 is shown. The first and second heating portions 28a, b may have first and second thermistor thermocouples 46a, b. The first and second heating portions 28a, b may additionally have first and second heaters 48a, b. The first and second thermocouples 46a, b and heaters 48a, b may be in electrical communication with the control module 24. When the operator turns on the control module 24, the control module 24 may send power to the heaters 48a, b to increase the temperature of the heating portions 50a, b. The thermocouples 46a, b take the reading of the temperature of the heating portions 50a, b and send that information to the control module 24. The temperature of the heating portions 50a, b may be displayed on the readout 40. If the thermocouple 46a, b indicates that the heating portions 50a, b have reached the maximum temperature set by the operator, then the control module 24 modulates the power supplied to the heaters 48a, b so that the temperature of the heating portions 50a, b is maintained at about the maximum temperature set by the operator.

Optionally, a temperature sensor 68 may be located adjacent the exit 36 of the heater 10, 10a. The sensor 68 may sense a temperature of the nutritional fluid flowing through the tube 14, 14a, 18 as the nutritional fluid flows out of the heater 10, 10a. The temperature sensor 68 may send a signal to the control module 24 which may be programmed to modulate power to the heater 10, 10a based on the sensed temperature of the nutritional liquid instead of the sensed temperature of the heating element 50a, b.

First and second insulators 52a, b may be disposed between the thermocouples 46a, b and the heating portions 50a, b. The heating portions 50a, b may be a Kapton (i.e., polyimide) heater. The heating portions 50a, b may have a curved semi-cylindrical configuration as shown in FIG. 4. Heat sinks 54a, b may be disposed on the inside of the heating portions 50a, b. The heat sinks 54a, b may define the straight grooves 34a, b of the first and second heating portions 28a, b. The straight grooves 34a, b may have a semi-circular cross sectional configuration so as to receive the tube 14, 14a and 18 which preferably has a cylindrical cross section. The back side 56a, b may have a curved configuration and receive the heating portions 50a, b. The heating portions 50a, b may be mounted to the back sides 56; b of the heating portions 50a, b through methods known in the art or developed in the future.

The heaters 48a, b, the heat sinks 54a, b, the insulation 52a, b and the thermocouples 46a, b may all be mounted within respective outer cases 58a, b. The outer cases 58a, b may have first and second hinge elements 60; b. The hinge elements 60a, b may be nested together and held together by pin 62. A torsion spring 63 may be mounted to the hinge elements 60a, b to bias the heating portions 28a, b to the closed position. The outer cases 58a, b may additionally have support members 64a, b that are received into the first and second handles 26a, b for mounting the outer cases 50a, b to the handles 26a, b.

Figure 5:
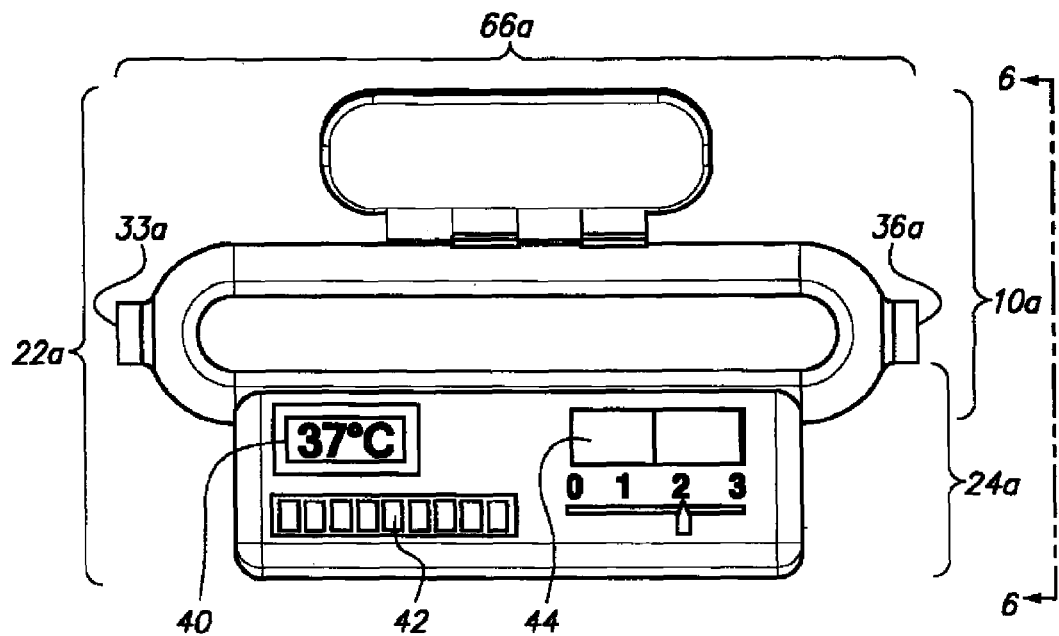
FIG. 5 is an illustration of a second embodiment of the heating system with the control module integrated into the heater.
Figure 6:
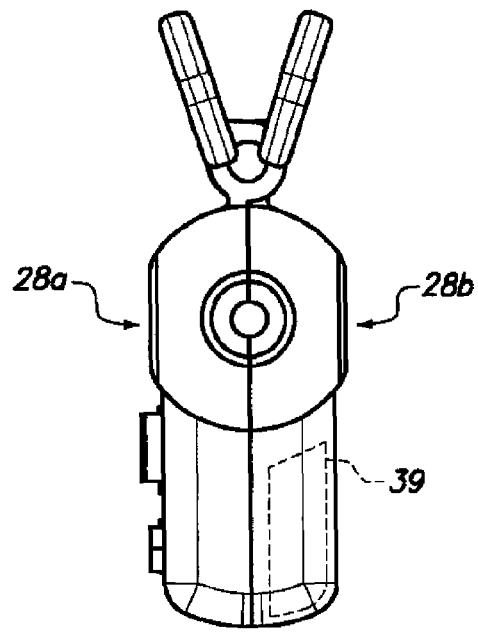
FIG. 6 is a side view of the second embodiment of the heating system shown in FIG. 5.

Referring now to FIGS. 5 and 6, a second embodiment of the heating system 22a is shown. The heating system 22a has a heater 10a and a control module 24a which are integrated to each other. As shown in FIG. 6, the control module 24a may be integrated into one or both of the heating portions 28a, b. The control module 24a may have the readout 40, indicator 42 and on/off switch 44 integrated into the first heating portion 28a. Battery pack 39 may be integrated into the second heating portion 28b. The electronics for the readout 40, indicator 42 and the on/off switch 44 may be in electrical communication with the battery pack 39. Moreover, the battery pack 39 may be in electrical communication with the heater 48a, b and the thermocouple 46a, b mounted within the outer cases 58a, b of the first and second heating portions 28a, b. The heating system 22a may operate in substantially the same manner as that described in relation to heating system 22 except that the control module 24 is integrated into the heater 10a.

The heater 10, 10a discussed herein may be placed as close to the neonate 16 as possible. This does not mean that the heater 10, 10a is placed on the tube 14, 14, 18 away from the neonate and the tube 14, 14a, 18 is bent so that the heater 10, 10a is located closely adjacent to the heater 10, 10a. Instead, this means that the distance that the nutritional liquid fluid flows from the heater 10, 10a to the neonate 16 through the tube 14, 14a, 18 is minimized by placing the heater 10, 10a as close to the neonate along a length of the tube 14, 14a, 18. The extension tube 18, feeding tube 14, 14a have a linear length. The heater 10, 10a may be placed on the tube 14, 14a, 18 at any position along the length of the tube 14, 14a, 18. However, as discussed herein it is advantageous that the heater 10, 10a be placed near the neonate 16 along the length of the tube 14, 14a, 18. By placing the heater 10, 10a closer to the neonate 16 the distance that the nutritional liquid travels to reach the neonate 16 after the nutritional liquid exits the heater 10, 10a is minimized so that heat loss through the tube is negligible. For example, after the nutritional liquid exits the heater 10, 10a the heat in the nutritional liquid begins to be transferred to the environment thereby cooling the nutritional liquid. By the time the nutritional liquid reaches the neonate 16, the nutritional liquid has a lower temperature than when the nutritional liquid exited the heater 10, 10a. Nonetheless, the nutritional liquid is above room temperature and is preferably about equal to the body temperature of. If the temperature drop from the heater 10, 10a to the neonate 16 is significant, it is contemplated that the heater 10, 10a may raise the temperature of the nutritional liquid to a temperature above the body temperature of a human. In this manner, as the nutritional liquid flows from the heater 10, 10*a* towards the neonate 16, the temperature of the nutritional liquid cools down to about the body temperature of a person.

The heater 10, 10*a* may be sufficiently long so that the nutritional liquid can be heated to the target temperature of the neonate. The heater 10, 10*a* has a particular length 66, 66*a* as shown in FIGS. 2 and 5. The nutritional liquid flows into the heater 10, 10*a* from the entrance 33,33*a* and leaves out of exit 36, 36*a*. However, the actual heating portions have a length 68 (see FIG. 4) which is shorter than the length 66 of the heater 10, 10*a*. The heater 10, 10*a* is mounted to a heat conductor 54*a, b*. The heat conductors 54*a, b* heat up the nutritional liquid flowing through the tube 14, 14*a*, 18. A length 70 of the heat conductor 54*a, b* defines a heating region which heats up the nutritional liquid flowing through the tube 14, 14*a*, 18. The heating region may be sufficiently long to gradually raise the temperature of the nutritional liquid. If the length 70 of the heating region is too short, then the temperature of the nutritional liquid must be raised at a rapid rate which may require the heating portions 50*a, b* to be set at a high temperature. In this case, the nutritional liquid may be exposed to excessively high temperatures that may destroy immunological properties of the nutritional liquid. Accordingly, the length 70 of the heating region is sufficiently long so that the maximum temperature of the heating portions 50*a, b* may be reduced to a temperature which is safe for the nutritional liquid and can still raise the temperature of the nutritional liquid to the target temperature (e.g., body temperature, temperature above body temperature) at a reasonable rate.

As discussed herein the grooves 34*a, b* of the heating portions 28*a, b* that receive the tube 14, 14*a*, 18 may be straight. However, other shapes are also contemplated. By way of example, other shapes include but is not limited to Z shaped, L shaped, U shaped.

Figure 7:
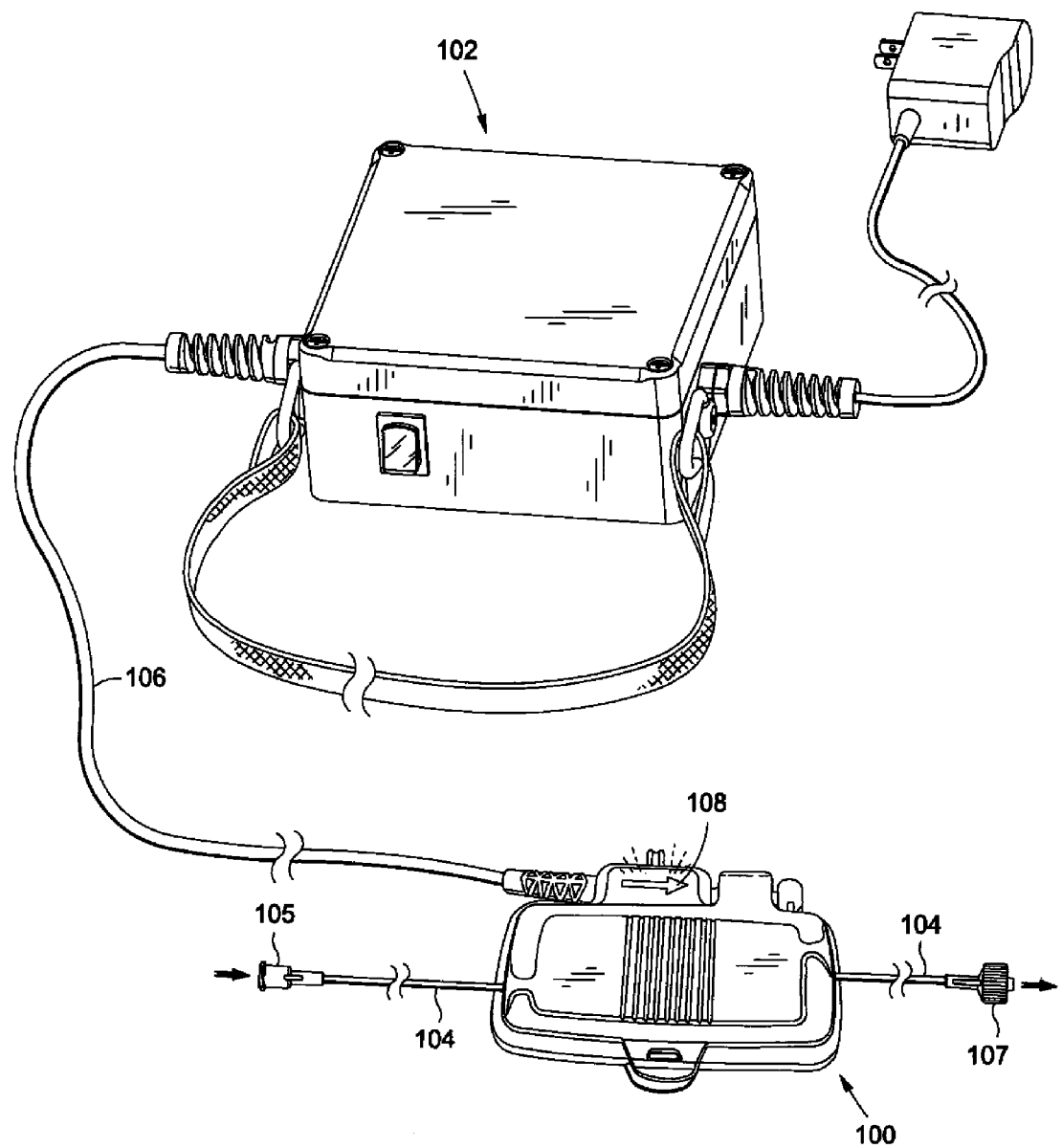
FIG. 7 is an illustration of a third embodiment of the heating system.
Figure 8:
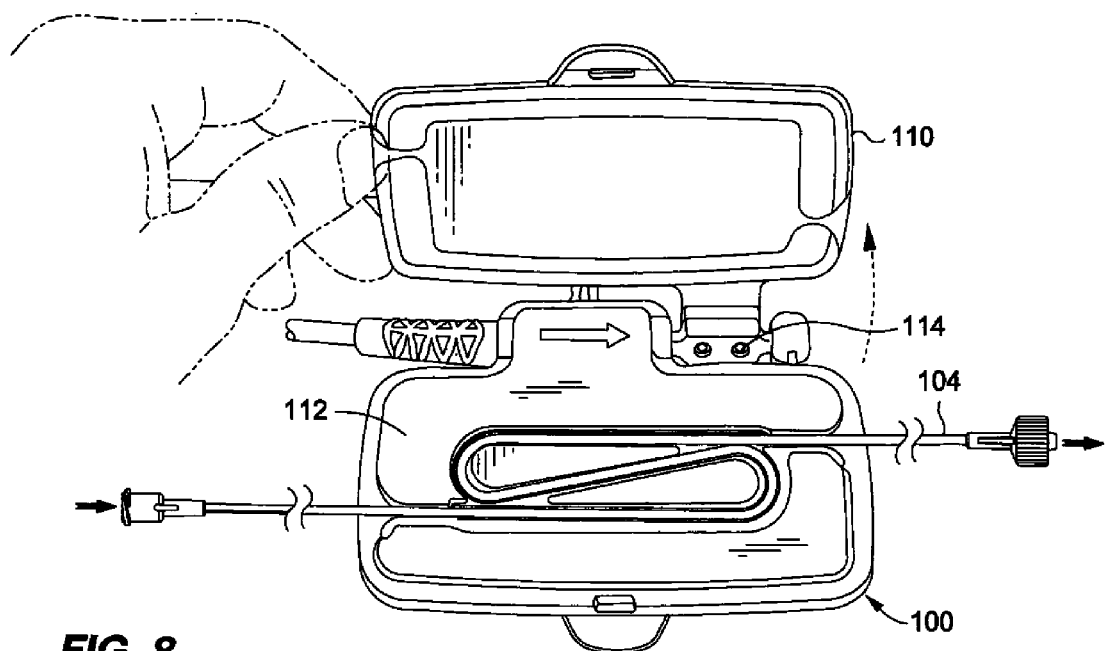
FIG. 8 is a perspective view of the third embodiment of the heating system showing the heater opened with a serpentine shaped feeding tube module in place.
Figure 9:
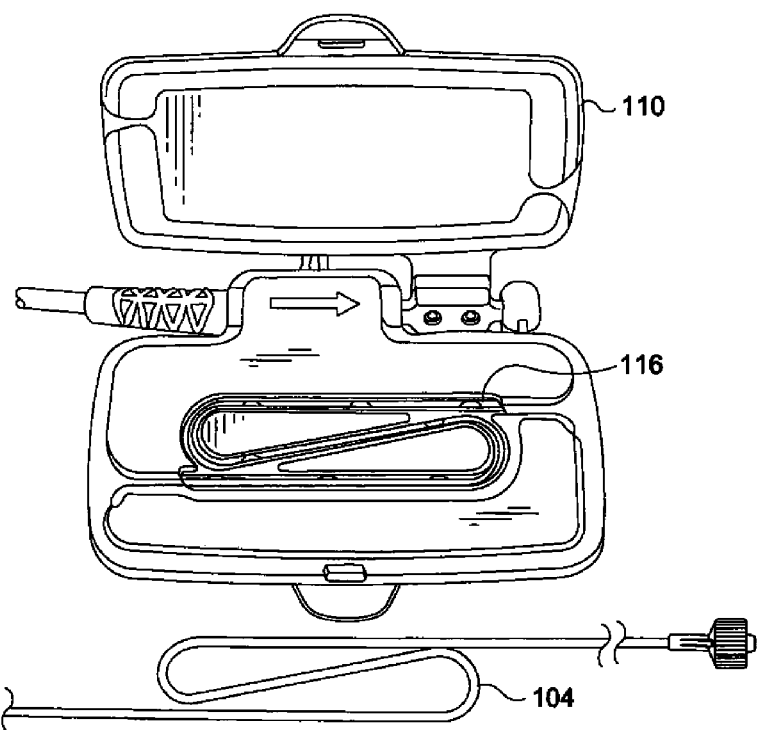
FIG. 9 is a perspective view of FIG. 8 with the serpentine shaped feeding tube module removed.

Referring now to FIGS. 7-10, a third embodiment of the heating system is shown. This embodiment includes a heater 100 and a control module 102. As shown in FIGS. 8 and 9, this embodiment includes a feeding tube module 104 having a serpentine shaped feeding tube configuration capable of being inserted into the heater 100. In particular, the feeding tube module 104 may be disposed proximal to a heating portion 112 of the heater. More particularly, the heating portion 112 may feature corresponding serpentine shaped grooves 116, into which the feeding tube module 104 is inserted. While FIGS. 8 and 9 show the serpentine feeding tube module 104 as having two curve portions, thus creating a path with three straight portions within the heating portion 112, it is contemplated that this is just one example and various shapes and flow paths may be envisioned for use. The benefit of using a serpentine shaped feeding tube module, is that the nutritional liquid spends an extended period of time within the heating portion 112, in comparison to a straight path. By extending the period of time within the heating portion 112, the nutritional liquid may be heated using an overall lower temperature, thereby preventing heat degradation of the nutritional liquid from extreme temperatures, while also maintaining the ability of allowing the nutritional liquid to reach body temperature. As such, the use of the terms "serpentine" or "serpentine shaped" in intended to encompass configurations that extend the flow path of the feeding tube within the heating portion. For example, additional configurations that could be utilized are Z-shaped configurations, zigzag configurations, and other configurations that extend the length of the feeding tube flow path within the heating portion.

The feeding tube module 104 is formed to correspond in shape and design to the serpentine shaped grooves 116 formed in the heater 100, so that the feeding tube module 104 may be quickly and easily placed directly into, and registered within, the grooves 116. Additionally, the feeding tube module 104 has a proximal connector 105 on one end and a distal connector 107 on the opposite end. The proximal connector 105 may be attachable to a source of nutritional liquid, while the distal connector may be attachable to a feeding tube placed within the patient. The feeding tube module 104 may be formed of any suitable material or polymer that is both medical grade and that will retain the serpentine shape during use and under heat.

As seen in FIG. 7, the heater 100 is electrically connected with the control module 102 via a control cable 106. Additionally, the heater 100 may include an operating indicator 108 that illuminates when the heater cover 110 is closed and the heater 100 is operational. The operating indicator 108 may be enabled by the closing of a microswitch 114. In particular, the microswitch may be positioned within the heater 100 in such a fashion that it is depressed by the closing of the heater cover 110, such that the operating indicator 108 will not illuminate and the heater heating portion 112 will not begin heating unless the heater cover 110 is in a fully closed position. This prevents raising the temperature of the heating portion 112 while the cover 110 is in an open position, thereby reducing the possibility of burn injuries by users of the heater 100 and allows users to visually confirm the heater is operating by viewing the illuminated operating indicator 108.

Figure 10:
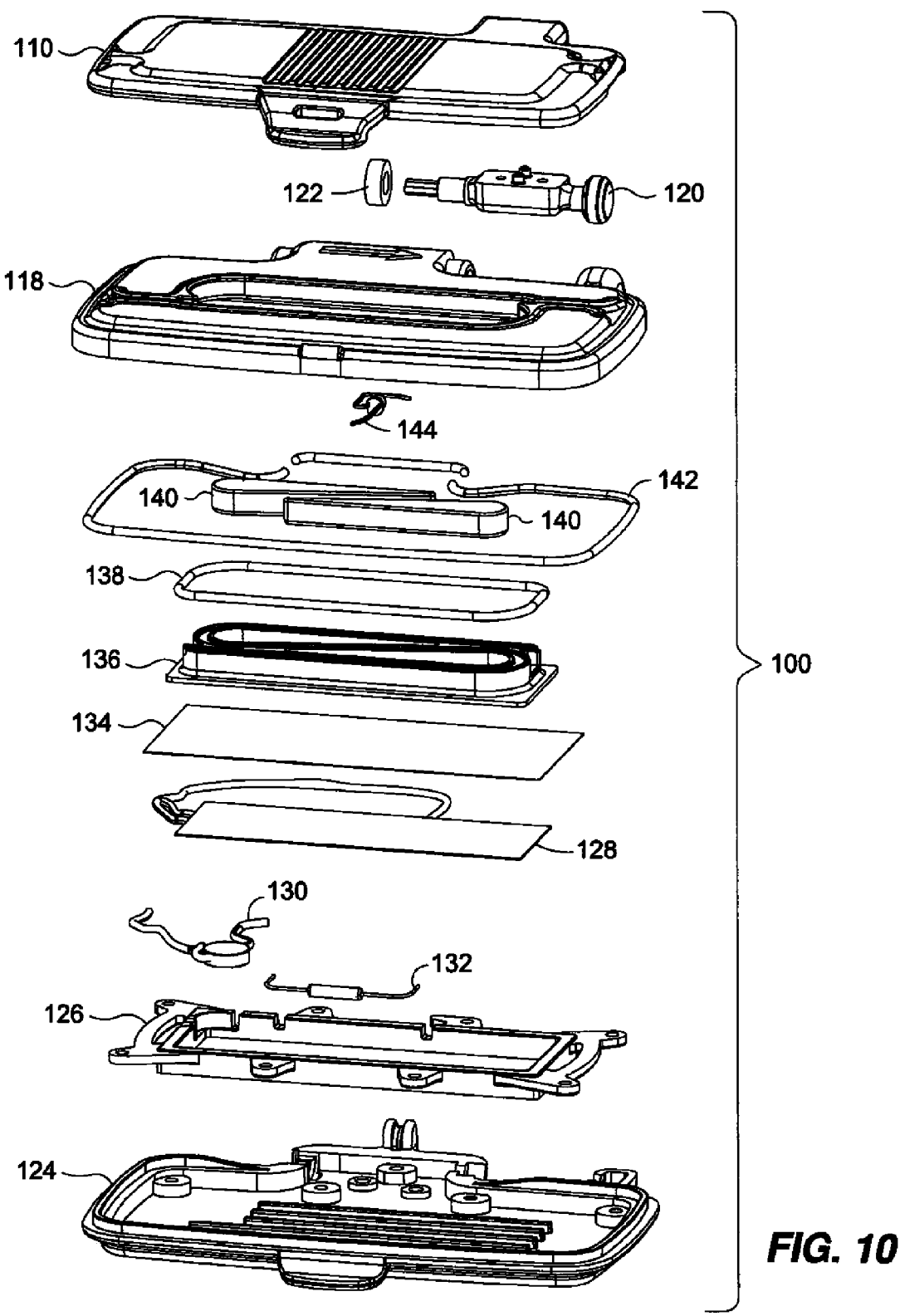
FIG. 10 is an exploded perspective view of the heater shown in FIGS. 7-9.

Referring now to FIG. 10, an exploded view of the heater 100 is shown. As can be seen, the heater cover 110 may be rotatably attached to a heater case 118 by way of a cam mount 120. In particular, the heater case 118 may cover the majority of internal components of the heater 100, and also features the serpentine shaped grooves 116 into which the feeding tube module 104 is inserted during use. The cam mount 120 may have a rotating portion so that the heater cover 110 may be lifted and lowered in relation to the heater case 118 during use. Furthermore, the microswitch 114 may be disposed within the cam mount 120, so that when the heater cover 110 is lifted, operation of the heater 100 ceases as the cover 110 is no longer in contact with the microswitch 114. Conversely, as the heater cover 110 is lowered into position for use, it may depress the microswitch 114 thereby activating the heater 100 and the operating indicator 108. Additionally, the heater 100 may include an illumination source 144, for example an LED, positioned below the operating indicator 108, such that when the heater cover 110 is closed and the heater 100 is operational, the illumination source 144 is illuminated to visually indicate the operation of the device. The cam mount 120 may further include a cable connector 122, such that the control cable 106 connects to the control module 102 on one end and the heater 100 on the other end by way of the cam mount 120 and cable connector 122.

The heater 100 further includes a heater base 124 located in a lowermost position that contains the majority of the internal heater components. It is envisioned that the heater cover 110, heater case 118, and heater base 124 may be fabricated out of suitable polymer plastic material, but may be made of metal or other materials. Located within, and directly attached to, the heater base 124 may be a heater clamp 126 to which is attached a heating unit 128. The heater 100 may further include a thermocouple 130 located proximally to the heating unit 128. The heating unit 128 and thermocouple 130 may be in electrical communication with the control module 102, such that when the heater 100 is activated the heating unit 128 receives power and increases the temperature of the heating portion 112 and the thermocouple 130 monitors the temperature of the heating portion 112 and conveys that information to the control module 102. The heater 100 may further include a thermal cutoff 132 in electrical communication with the heating unit 128. When the thermal cutoff 132 reaches a set temperature above normal operating conditions of the heater 100, the thermal cutoff 132 will trip, thereby eliminating the flow of power to the heating unit 128 and preventing an unsafe temperature during operation. While not shown in FIG. 10, it is contemplated that the electrical components described herein are connected in electronic communication with each other as would be readily understood and achieved by a person of ordinary skill in the art.

Figure 11:
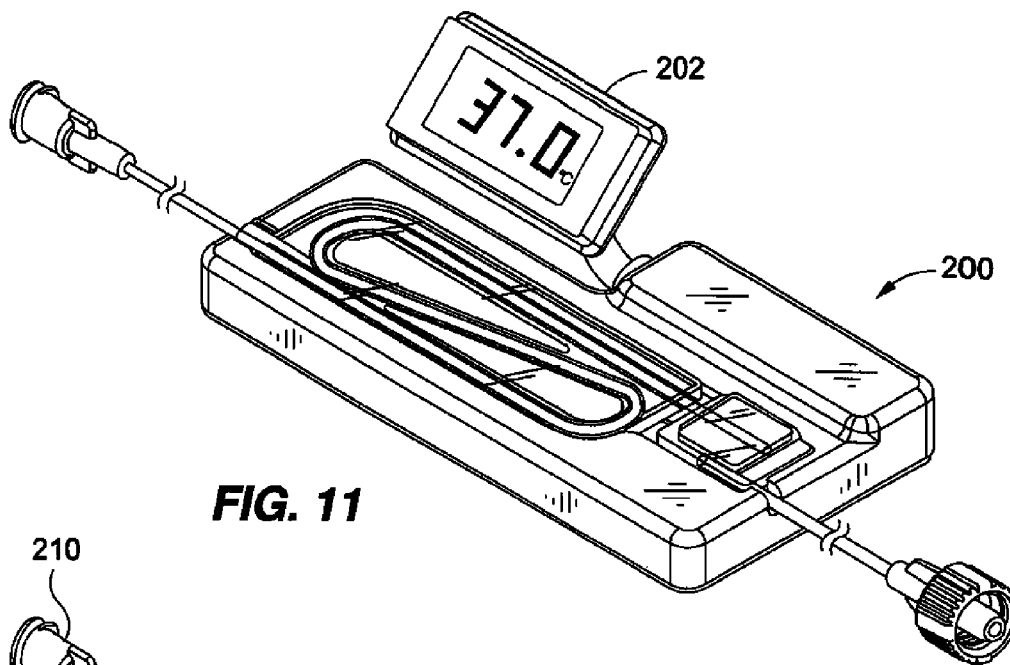
FIG. 11 is an illustration of a fourth embodiment of the heating system showing a feeding tube cassette in place.
Figure 12:
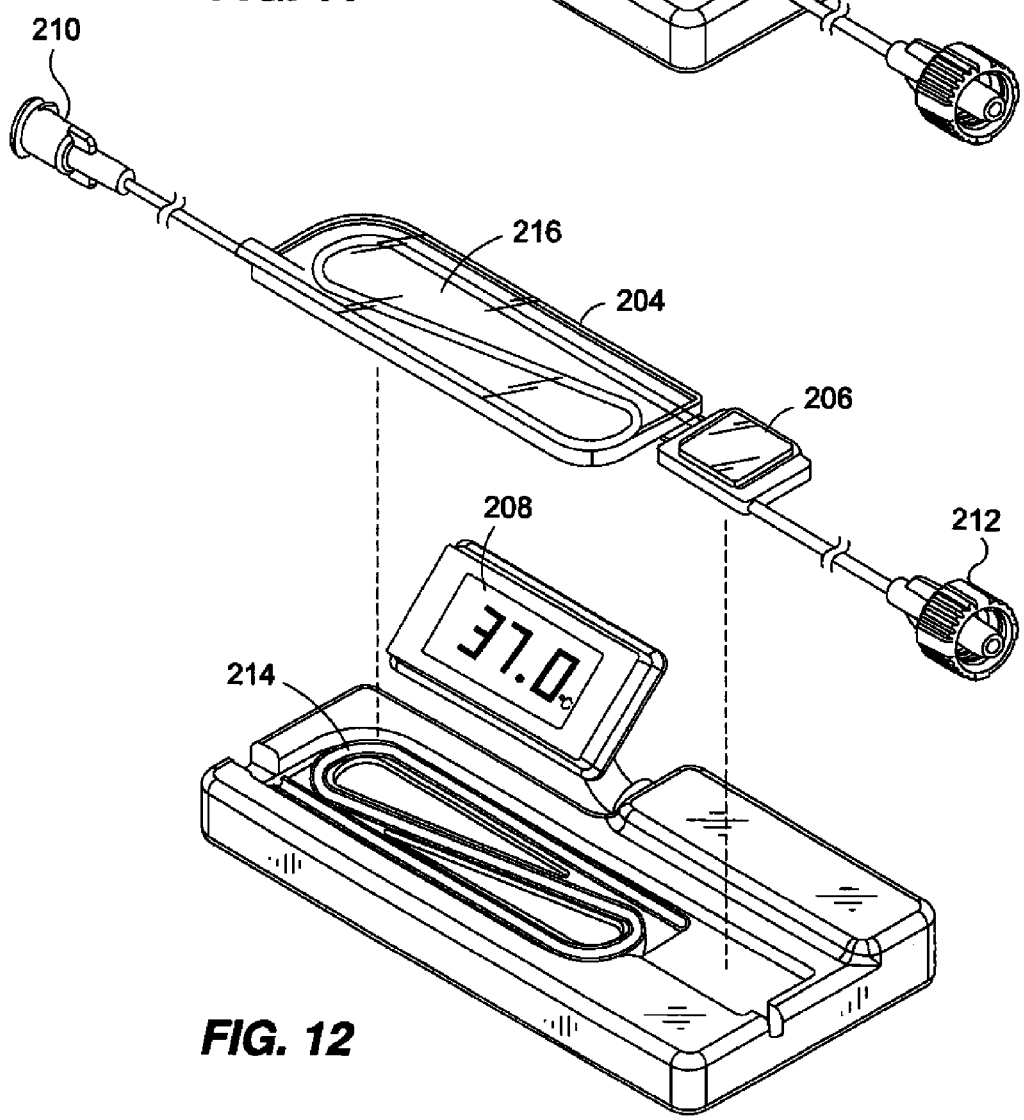
FIG. 12 is a perspective view of FIG. 12 with the feeding tube cassette removed.

While the heating unit 128 may take a substantially flat configuration, there may be attached to it a heat sink 136 into which the feeding tube module 104 is actually inserted. As such, the heat sink 136 may be formed to include a complementary shaped serpentine groove pattern to readily accept and register the feeding tube module 104. The heat sink 136 may be attached to the heating unit 128 by a polyimide tape 134. To avoid excess heat escape, the heat sink 136 may be surrounded by a heat sink O-ring 138, or other type of gasket, that seals any gap between the heat sink 136 and the heater case 118. As can be seen, the serpentine shape of the heat sink 136 fits and registers within the serpentine groove 116 of the heater case 118 to allow for insertion of the feeding tube module 104. Additionally, to prevent heat loss between the serpentine portions of the heat sink 136, inserts 140 may be inserted into the open spaces of the heat sink. Further, a case O-ring 142, or other type of gasket, may be positioned between the heater base 124 and the heater case 118 to prevent heat escape from the heater 100 and to prevent the entry of liquids from potential spills on the heater. Referring now to FIGS. 11-13, a fourth embodiment of the heating system is shown. As can be seen in FIG. 11, this embodiment is substantially similar to that discussed above as the third embodiment, with the exception that the control module 202 is integrated directly into the heater 200. This eliminates the need for a standalone control module, and allows for the input and monitoring of information to occur directly at the heater 200 by way of an integrated display 208, rather than on a separate control module connected by an electronic cable.

As is illustrated in FIGS. 14-17, it is contemplated that in place of the serpentine feeding tube module 104, as discussed above, one may use a serpentine feeding tube cassette 204 that may include an inline thermocouple 206 to directly monitor the temperature of the nutritional fluid as it exits the heater. In particular, the cassette 204 may include a proximal connector 210 on the entry side of the cassette 204 and a distal connector 212 on the opposite end of the cassette 204. The proximal connector 210 may be attachable to a source of nutritional liquid, while the distal connector 212 may be attachable to a feeding tube placed within the patient. Adjacent to the proximal connector 210 is the serpentine feeding tube configuration, while adjacent to the distal connector 212 is the thermocouple 206. As such, it can be seen that upon entry of the cassette 204, the nutritional liquid is heated as it moves through the serpentine feeding tube configuration placed within the serpentine shaped grooves 214 of the heater 200, and then the temperature of the nutritional liquid is monitored by the thermocouple 206 as it exits the cassette 204 via the distal connector 212. The thermocouple 206 may be in electrical communication with the control module 202 to monitor the temperature.

The cassette 204 differs from the serpentine feeding tube module 104, described above, in that it further includes a polymeric sheet 216 attached to the upper portion of the serpentine feeding tube portion. This sheet 216 operates to serve multiple functions. In particular, the sheet 216 maintains the serpentine feeding tube configuration rigidly in place to aid in the insertion of the cassette 204 into the heater serpentine grooves 214. Additionally, the sheet 216 aids in retaining heat within the serpentine feeding tube portion by creating a physical barrier to prevent heat loss. It is envisioned that both the feeding tube module 104 and the cassette 204 may be manufactured as disposable pieces, such that they are used for one feeding and then disposed of, rather than cleaned between uses of the heater.

The above description is given by way of example, and not limitation. Given the above disclosure, one skilled in the art could devise variations that are within the scope and spirit of the invention disclosed herein, including various ways of flow nutritional fluid through the tube 14, 14a, 18. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A system for heating neonate nutritional liquid so that a temperature of the nutritional liquid approximates a standard body temperature of a person during feeding, the system comprising:

a container for storage of the neonate nutritional liquid during feeding;

a tube defining first and second ends and a cartridge portion between the first and second ends, the first end of the tube connectable to the container and the second end disposable within a stomach of the neonate for routing the neonate nutritional liquid from the container to the neonate during feeding, the cartridge portion of the tube being preformed into a bent configuration and semi-rigid so that the cartridge portion of the tube retains the bent configuration when the cartridge portion of the tube is removed from a groove of a heater, and the tube being sufficiently rigid to maintain an open central lumen when the central lumen is empty;

the heater having a heating unit and a heat sink defining the groove of the heater wherein the groove is sized and configured to receive the bent cartridge portion of the tube for heating the neonate nutritional liquid as the neonate nutritional liquid flows from the container to the tube, the heater positioned at a minimal distance from the neonate during feeding to minimize heat loss during delivery of the neonate nutritional liquid.

2. The system of claim 1 wherein the cartridge portion of the tube has a zig zag configuration, Z shaped configuration, L shaped configuration, U shaped configuration or combinations thereof, and the configuration of the groove of the heater has the same configuration as the cartridge portion of the tube so that the cartridge portion of the tube is easily insertable into the groove of the heater.

3. The system of claim 2 wherein the zig zag configuration of the cartridge portion of the tube has a serpentine configuration.

4. The system of claim 1 further comprising a backing member with a first side of the cartridge portion of the tube attached to the backing member for rigidly fixing the bent configuration of the cartridge portion to facilitate insertion of the cartridge portion of the tube into the groove of the heater, and the groove of the heat sink having a corresponding bent configuration compared to the bent configuration of the cartridge portion of the tube so that the cartridge portion of the tube is easily insertable into the groove of the heat sink.

5. The system of claim 4 wherein the cartridge portion of the tube is disposable between the backing member and the heating unit so that the rigid backing aids in retaining heat within the cartridge portion.

6. The system of claim 4 wherein the rigid backing is a polymeric sheet or an insulation material.

7. The system of claim 1 further comprising a temperature sensor connected to the heating unit for sensing a temperature of the heating unit and sending a signal to a control module to cut off power to the heating unit when the temperature of the heating unit exceeds a preset upper limit.

8. The system of claim 1 wherein the heater has a heater base and a cover, the cover being traversable between a closed position and an opened position, the system further comprising a switch disposed adjacent to the cover so that in the closed position, the switch is depressed and operative to turn on a heater active signal, and in the opened position, the switch is released and operative to turn off the heater active signal.

9. The system of claim 8 wherein the heater active signal is a light.

10. A tube for use in a system for heating neonate nutritional liquid so that a temperature of the nutritional liquid approximates a standard body temperature of a person during feeding, the tube comprising:
an elongate body being sufficiently rigid to maintain an open central lumen when the central lumen is empty, the elongate body defining first and second ends and a cartridge portion between the first and second ends, the first end of the elongate body connectable to a container with the neonate nutritional liquid therein and the second end of the elongate body disposable within a stomach of the neonate for routing the neonate nutritional liquid from the container to the neonate during feeding, the cartridge portion of the elongate body being semi-rigid and preformed into a bent configuration, the cartridge portion being disposable in an internal cavity of a heater, the cartridge portion retains the bent configuration when the elongate body is removed from the heater, the cartridge portion being positioned at a minimal distance from the neonate to minimize heat loss during delivery of the neonate nutritional liquid.

11. The tube of claim 10 further comprising a sheet with a first side of the bent cartridge portion of the elongate body being attached to the sheet for rigidly fixing the bent configuration of the cartridge portion.

12. The tube of claim 10 wherein the cartridge portion is recessed within a groove formed on a side of the sheet.

13. The tube of claim 10 further comprises a temperature sensor attached to the elongate body downstream of the cartridge portion for reading a temperature of the neonate nutritional liquid after exiting the heater.

14. The tube of claim 10 wherein the tube further comprises an inline temperature sensor is mounted to the tube.

15. A system for heating neonate nutritional liquid so that a temperature of the nutritional liquid approximates a standard body temperature of a person during feeding, the system comprising:
a container for storage of the neonate nutritional liquid during feeding;
a tube defining a first end, a second end and a cassette, the first end of the tube being connectable to the container and the second end disposed within a stomach of the neonate for routing the neonate nutritional liquid from the container to the neonate during feeding, the cassette comprising a portion of the tube between the first and second ends having a preformed and semi-rigid bent configuration that retains the bent configuration and a backing member to retain the preformed bent configuration during manipulation of the cassette by a medical professional when the cassette is not disposed within an internal cavity of a heater, the tube being sufficiently rigid to maintain an open central lumen when the central lumen is empty;
the heater having a heating unit and a heat sink defining the internal cavity of the heater wherein the internal cavity is sized and configured to receive the cassette of the tube for heating the neonate nutritional liquid as the neonate nutritional liquid flows from the container to the neonate during feeding, the heater being positioned at a minimal distance from the neonate during feeding to minimize the heat loss during delivery of the neonate nutritional liquid.

16. The system of claim 15 wherein the internal cavity is a groove having a corresponding configuration to the preformed bent configuration of the cassette of the tube.

17. The system of claim 15 wherein the backing member is a polymeric material.

18. A system for heating neonate nutritional liquid so that a temperature of the nutritional liquid approximates a standard body temperature of a person during feeding, the system comprising:
a container for storage of the neonate nutritional liquid during feeding;
a tube defining a first end, a second end and a cassette, the first end of the tube being connectable to the container and the second end disposed within a stomach of the neonate for routing the neonate nutritional liquid from the container to the neonate during feeding, the cassette comprising a portion of the tube between the first and second ends having a semi rigid and preformed bent configuration and a backing member attached to one side of the portion of the tube so that the portion of the tube retains its bent configuration when the portion is removed from a groove of a heater, the tube being sufficiently semi rigid to maintain an open central lumen of the tube when the central lumen is empty;
the heater having a heating unit and a heat sink defining a groove of the heater wherein the groove is sized and configured to receive the portion of the tube having the prebent configuration for heating the neonate nutritional liquid as the neonate nutritional liquid flows from the container to the neonate during feeding and the back member retains the heat from the heating unit in the portion of the tube having the prebent configuration, the heater being positioned at a minimal distance from the neonate during feeding to minimize heat loss during delivery of the neonate nutritional liquid;
wherein the portion of the tube between the first and second ends having the preformed bent configuration retains the preformed bent configuration so that the portion retains the preformed bent configuration when the tube is removed from the heater.

19. The system of claim 18 further comprising:
a thermal cutoff switch electrically connected to the heating unit, the thermal cutoff switch monitors a temperature of the heating unit and shuts off power to the heating unit when the temperature of the heating unit exceeds a preset upper limit.

20. A system for heating neonate nutritional liquid so that a temperature of the nutritional liquid approximates a standard body temperature of a person during feeding, the system comprising:
a container for storage of the neonate nutritional liquid during feeding;
a tube defining first and second ends, the first end of the tube connectable to the container and the second end disposable within a stomach of the neonate for routing the neonate nutritional liquid from the container to the neonate during feeding, the tube defining a cartridge portion which is semi-rigid, the cartridge portion of the tube having a serpentine configuration which is retained when the cartridge portion of the tube is removed from an internal cavity of a heater, the tube being sufficiently rigid to maintain an open central lumen when the central lumen is empty;
the heater having a heating unit and a heat sink defining the internal cavity of the heater wherein the internal cavity is sized and configured to receive the cartridge portion of the tube for heating the neonate nutritional liquid as the neonate nutritional liquid flows from the container to the neonate during feeding, the heater being positioned at a minimal distance from the neonate during feeding to minimize heat loss during delivery of the neonate nutritional liquid;
an inline thermocouple mounted to the tube downstream of the heating unit when the tube is received in the internal cavity of the heat sink.

21. The system of claim 20 wherein the heater has a second cavity for receiving the inline thermocouple.

\* \* \* \* \*